(12) United States Patent
Hewitt

(10) Patent No.: US 7,854,899 B2
(45) Date of Patent: Dec. 21, 2010

(54) TEMPLATE METHODS AND DEVICES FOR PREPARING SAMPLE ARRAYS

(75) Inventor: Stephen M. Hewitt, Potomac, MD (US)

(73) Assignee: The United States of America as represented by the Secretary of Health and Human Services, Rockville, MD (US)

( * ) Notice: Subject to any disclaimer, the term of this patent is extended or adjusted under 35 U.S.C. 154(b) by 707 days.

(21) Appl. No.: 10/928,656

(22) Filed: Aug. 26, 2004

(65) Prior Publication Data

US 2006/0046282 A1 Mar. 2, 2006

(51) Int. Cl.
*B01L 9/00* (2006.01)
(52) U.S. Cl. .......................... 422/104; 422/102; 422/99
(58) Field of Classification Search .................. 422/104, 422/102, 99
See application file for complete search history.

(56) References Cited

U.S. PATENT DOCUMENTS

| | | | |
|---|---|---|---|
| 4,684,613 A | 8/1987 | Barrere et al. | |
| 4,820,504 A | 4/1989 | Battifora | |
| 4,914,022 A | 4/1990 | Furmanski et al. | |
| 5,002,377 A | 3/1991 | Battifora et al. | |
| 5,061,452 A * | 10/1991 | Yamamoto et al. | 422/101 |
| 5,307,262 A | 4/1994 | Ertel | |
| 5,355,439 A | 10/1994 | Bernstein et al. | |
| 5,614,415 A | 3/1997 | Markin | |
| 5,675,715 A | 10/1997 | Bernstein et al. | |
| 5,695,537 A | 12/1997 | Sykes | |
| 5,700,637 A | 12/1997 | Southern | |
| 5,746,855 A | 5/1998 | Bolles | |
| 5,843,700 A * | 12/1998 | Kerrod et al. | 435/40.5 |
| 5,843,767 A | 12/1998 | Beattie | |
| 5,882,864 A | 3/1999 | An et al. | |
| 5,930,461 A | 7/1999 | Bernstein et al. | |
| 6,004,755 A | 12/1999 | Wang | |

(Continued)

FOREIGN PATENT DOCUMENTS

GB 2 197 471 5/1998

(Continued)

OTHER PUBLICATIONS

Hewitt, Methods in Molecular Biology (2004), vol. 264, pp. 61-72.*

(Continued)

*Primary Examiner*—Natalia Levkovich
(74) *Attorney, Agent, or Firm*—Klarquist Sparkman, LLP

(57) ABSTRACT

A method for preparing a microarray that includes placing at least one template over a first surface of the recipient block, wherein the template defines an array of openings and the recipient block has a plurality of receptacle holes, such that the array of openings are aligned with the plurality of receptacle holes. A needle or punch that contains a sample is inserted through the openings of the template. The sample then is inserted into the receptacle hole in the recipient block. A device is also disclosed that includes a platform defining (i) a first surface, and (ii) a first region configured to retain at least one recipient block; and a raised template defining an array of openings, secured to the first surface of the platform and positioned above the first region configured to retain the recipient block.

16 Claims, 2 Drawing Sheets

U.S. PATENT DOCUMENTS

| | | | |
|---|---|---|---|
| 6,084,991 | A | 7/2000 | Sampas |
| 6,103,192 | A | 8/2000 | Stapleton |
| 6,103,518 | A | 8/2000 | Leighton |
| 6,136,592 | A | 10/2000 | Leighton |
| 6,291,163 | B1 | 9/2001 | Sidransky |
| 6,383,801 | B1 | 5/2002 | Leighton |
| 6,699,710 | B1 | 3/2004 | Kononen et al. |
| 6,852,289 | B2 * | 2/2005 | Gordon et al. ............... 422/101 |
| 2002/0192702 | A1 | 12/2002 | Kononen et al. |
| 2003/0054342 | A1 | 3/2003 | Star et al. |
| 2003/0138827 | A1 | 7/2003 | Kononen et al. |
| 2003/0157523 | A1* | 8/2003 | Frantz et al. ................... 435/6 |
| 2003/0213906 | A1* | 11/2003 | Lennon et al. ............... 250/288 |
| 2003/0215936 | A1 | 11/2003 | Kallioniemi et al. |
| 2005/0260745 | A1* | 11/2005 | Domansky et al. ........ 435/294.1 |

FOREIGN PATENT DOCUMENTS

| | | |
|---|---|---|
| WO | WO 98/44333 | 10/1998 |
| WO | WO 99/30264 | 7/1999 |
| WO | WO 99/44062 | 9/1999 |
| WO | WO 99/44063 | 9/1999 |

OTHER PUBLICATIONS

Barlund et al., *Genes Chrom. Cancer* 20:372-376 (1997).
Battifora et al., *Lab. Invest.* 55:244-248 (1986).
Battifora and Mehta, *Lab. Invest.* 63:722-724 (1990).
Bubendorf et al., *Cancer Res.* 59(4):803-806 (1999).
Den Dunnen et al., *Human Mutation.* 14(2):95-102 (1999).
Eisen et al., *Current Opinion in Oncology* 10:486-491 (1998).
Enghardt et al., *The Journal of Histotechnology* vol. 18(1):51-55, 1995.
Faderl et al., *N. Engl. J. Med.* 341:164-172 (1999).
Gillett et al., *J. Pathol.* 192:549-553, 2000.
Green and Olson, *PNAS USA* 87:1213-1217 (1990).
Hidalgo et al., *J. Clin. Pathol.* 56:144-146, 2003.
Kallioniemi et al., *Science* 258:818-821 (1992).
Kononen et al., *Nature Medicine* 4:844-847 (1998).
Kraaz et al., "Multiblock: an aid in diagnostic immunohistochemistry," *J. Clin. Pathol.* 41:1377 (1988).
Lampkin et al., *The Journal of Histotechnology* 13(2):121-123, 1990.
Lantuejoul et al., *Am. J. Surg. Pathol.* 22(10):1267-1276 (1998).
Levéen et al., *Experimental Cell Research* 207:283-289, 1993.
Liang et al., *Science* 257:967-972 (1992).
Miller and Groothuis, *Am. J. Clin. Pathol.* 96:228-232 (1991).
Moch et al., *Hum. Pathol.* 28:1255-1259 (1997).
Moch et al., *Am. J. Pathol.* 154(4):981-986 (1999).
Moore et al., *Molecular Biotechnology* 14(2):89-97 (2000).
Press et al., *Cancer Research* 54:2771-2777, 1994.
Press et al., *Journal of Clinical Oncology* 15(8):2894-2903, 1997.
Pretlow et al., *J. Natl. Cancer Inst.* 3:394-398 (1993).
Ramsay, *Nature Biotechnol.* 16:14-44 (1998).
Schena et al., *Science,* 270:467-470 (1995).
Schena, *BioEssays,* 18(5):427-431 (1996).
Schraml et al., *Clin. Cancer Res.* 5(8):1966-1975 (1999).
Service, *Science,* 282:396-399 (1998).
Soares, *Cur. Opp. In Biotechnol.* 8:542-546 (1997).
Sundblad, *Am. J. Clin. Pathol.* 102:192-193 (1993).
Tanner et al., *Cancer Res.* 54:4257-4260 (1994).
Velculescu et al., *Science* 270:484-487 (1995).
Wan et al., *J. Immunol. Meth.* 103:121-129 (1987).
Wimmer et al., *Human Mutation.* 16(1):90-91 (2000).
"Cassette MicroWriter 2," http://www.unitedbiosciences.com.au/Content/Products/Cassette_MicroWriter_2.html, 2004.
"Paraffin Tape-Transfer System," http://www.instrumedics.com/PSA.htm, 2002.

* cited by examiner

TEMPLATE METHODS AND DEVICES FOR PREPARING SAMPLE ARRAYS

FIELD

This disclosure relates to methods and devices for making arrays of samples.

BACKGROUND

Advances in medical research and the successful development of new, improved diagnostic tools and therapeutic agents are often dependent on the ability to screen thousands of clinical samples for molecular markers in a high-throughput fashion. Tissue microarrays can include hundreds or even thousands of tiny discs (approximately 1 mm in diameter, for example) of tissue specimens, fixed and arranged on a single microscopic slide. Currently available arraying tools provide means to generate thousands of copies of this kind of slide.

However, the equipment currently available to make tissue microarrays can be quite complex and expensive (especially the automated tools), and thus is often beyond the resources of many researchers. Thus, a need continues to exist for inexpensive, simple techniques and devices for making tissue microarrays.

SUMMARY

Disclosed herein is a method for preparing a microarray that includes placing at least one template over a first surface of the recipient block, wherein the template defines an array of openings and the recipient block has a plurality of receptacle holes, such that the array of openings are aligned with the plurality of receptacle holes. A needle or punch that contains a sample is inserted through the openings of the template. The sample then is inserted into the receptacle hole in the recipient block.

Also disclosed herein is another embodiment for preparing a microarray that includes placing a first template over a first surface of a recipient block, wherein the first template defines a first array of first openings. A first punch or needle then is inserted through at least one opening in the first template so as to bore a receptacle hole in the recipient block. A second template is placed over the first template, wherein the second template defines a second array of second openings, such that the first openings and the second openings are aligned axially. A second punch or needle is inserted through at least the second opening such that the second punch or needle does not penetrate a plane of the first surface of the recipient block. A sample then is inserted via the second punch or needle into the receptacle hole in the recipient block.

A construct that can be used in the methods disclosed herein is also provided wherein the construct includes a recipient block defining an array of receptacle holes; and at least one template attached to a first surface of the recipient block, the template defining an array of openings that are complementary with the array of receptacle holes in the recipient block.

Also described herein is a device for preparing an array of samples that includes a platform defining (i) a first surface, and (ii) a first region configured to retain at least one recipient block. A raised template defining an array of openings is secured to the first surface of the platform and positioned above the first region configured to retain the recipient block.

BRIEF DESCRIPTION OF THE FIGURES

The methods, constructs and devices disclosed herein will be described with reference to the accompanying drawing wherein.

DETAILED DESCRIPTION OF SEVERAL EXAMPLES

Figure 1:
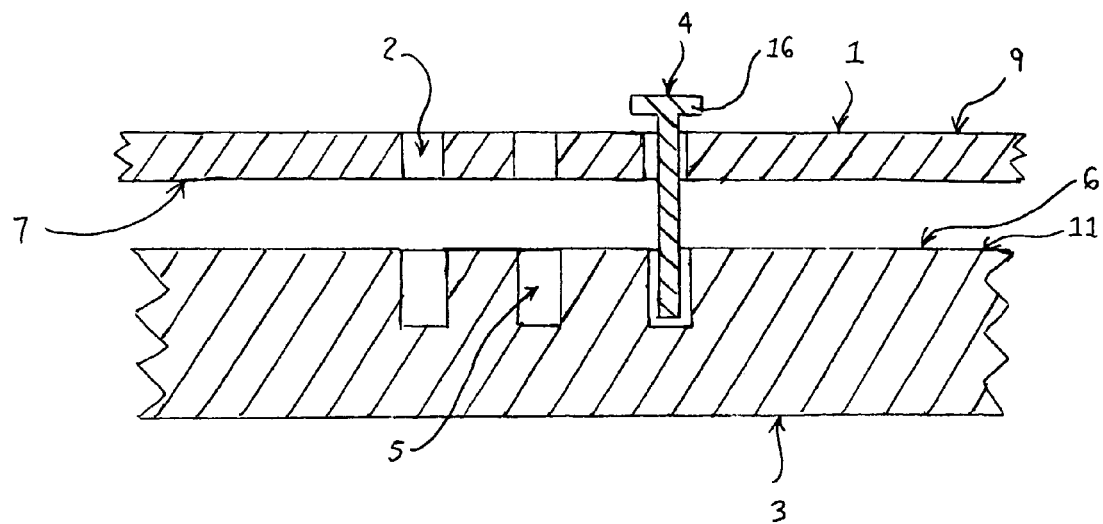
FIG. 1 is a cross-sectional view of one example of the template disclosed herein.

For ease of understanding, the following terms used herein are described below in more detail:

An "array" is an arrangement of samples, such as biological macromolecules (e.g., polypeptides or nucleic acids), cell samples, tissue samples, geological samples (including dirt), or plant samples, in addressable locations on or in a substrate. The array may be regular (arranged in uniform rows and columns, for instance) or irregular. The number of addressable locations on the array can vary, for example from a few (such as three) to more than 50, 100, 200, 500, 1000, 10,000, or more.

A "cryoarray" refers to an array of samples, such as biological samples, placed into a block of substrate (such as embedding compound) at addressable locations, which loaded block is then sliced (sectioned) to produce a plurality of sequential cryosections, each containing a portion of the samples in the block. The samples may "freeze" into the block of substrate, such that the loaded block can be sectioned and will maintain the portions of sample in addressable locations that correlate to the locations of the samples in the loaded block. Examples of cryoarrays include protein cryoarrays (in which the samples contain one or more known or unknown proteins), and nucleic acid cryoarrays (in which the samples contain one or more known or unknown nucleic acids). Additional non-limiting examples of cryoarrays are discussed herein.

"Freezing" and "frozen" as they are used herein refers to the solidification of a liquid or fluid sample, to a point of solidity (rigidity) sufficient that it can be sectioned or sliced. Freezing usually occurs at a temperature at or below the freezing temperature of water, but where the sample contains constituents other than water, the "freezing" (solidification) point may be substantially different from 0° C.

A "microarray" is an array that is miniaturized such that microscopic examination may be required for visual evaluation.

A "tissue specimen or sample" refers to an intact piece of tissue, for example embedded in a medium or a portion taken from an intact piece of tissue. A tissue specimen or sample may also be a liquid cellular suspension.

The above term descriptions are provided solely to aid the reader, and should not be construed to have a scope less than that understood by a person of ordinary skill in the art or as limiting the scope of the appended claims.

The singular terms "a," "an," and "the" include plural referents unless context clearly indicates otherwise. Similarly, the word "or" is intended to include "and" unless the context clearly indicates otherwise. The word "comprises" indicates "includes."

The above-described methods and devices provide a simplified, less expensive technique for making arrays of samples, especially biological specimens (e.g., tissue microarrays). An example of a tissue microarray block is shown in FIGS. 4-7 of U.S. Pat. No. 6,699,710. Expensive and complex apparatus such as micrometer motion devices are not necessarily required to practice the methods described herein (although they can be used in conjunction with the template(s) if desired). The template(s) method is easy-to-use and can produce multiple accurate replicates of tissue microarrays.

In general, at least one template is used as a needle or punch guide for introducing samples into the receptacle holes formed in a recipient block. In one embodiment disclosed herein, the template is used as a needle or punch guide for boring receptacle holes in a recipient block, and then as a needle or punch guide for introducing samples into the receptacle holes. In another embodiment disclosed herein, an already-formed recipient block having a plurality of receptacle holes may be provided and then a template is used as a needle or punch guide for introducing samples into the receptacle holes. An illustrative example of the disclosed methods is described herein with reference to FIGS. 1 and 2.

With reference to FIG. 1, a template 1 is provided that defines a plurality of openings 2. The openings 2 extend through the full width of the template 1 from a top surface 9 of the template 1 to a bottom surface 7 of the template 1. The template 1 is arranged above a first surface 6 of a recipient block 3. The bottom surface 7 of the template 1 may, or may not, contact the first surface 6 of the recipient block 3. For example, the bottom surface 7 of the template may be provided with a raised edge (not shown in FIG. 1) along its periphery that raises the template 1 off of the first surface 6 of the recipient block 3. The template 1 and/or the recipient block 3 may be provided with an attachment mechanism such as a clamp to securely engage the template 1 with the recipient block 3 in an aligned position. Alternatively, adhesive tape may be applied to the template 1 and the recipient block 3 to releasably secure the template 1 to the recipient block 3.

A hollow punch or needle 4 is inserted into an opening 2 so that it penetrates into the recipient block 3 and bores a core element from the recipient block 3. The opening 2 serves as a guide for the proper placement and direction of the hollow punch or needle 4. The core element located within the hollow of the punch or needle 4 then is removed by withdrawing the punch or needle 4 back through the opening 2. Removal of the core element results in the formation of a receptacle hole 5. A plurality of receptacle holes 5 can be formed in the recipient block 3 that are complementary to (i.e., aligned with) the respective openings 2 in the template 1 by repeating the above-described method.

Once the receptacle holes 5 are formed in the recipient block 3, biological specimens such as tissue samples may be inserted into the receptacle holes 5. The template 1 remains in place over the recipient block 3 in order to insert the tissue samples. A punch or needle that holds a tissue sample (which may be the same or different from the punch or needle used to bore the receptacle holes) is inserted through the opening 2. Typically, the punch or needle does not penetrate a plane 11 of the first surface 6 of the recipient block 3. A stylet 12 (see FIG. 2) disposed within the hollow channel of the needle or punch then is advanced to expel or eject the tissue sample from the needle or punch.

Figure 2:
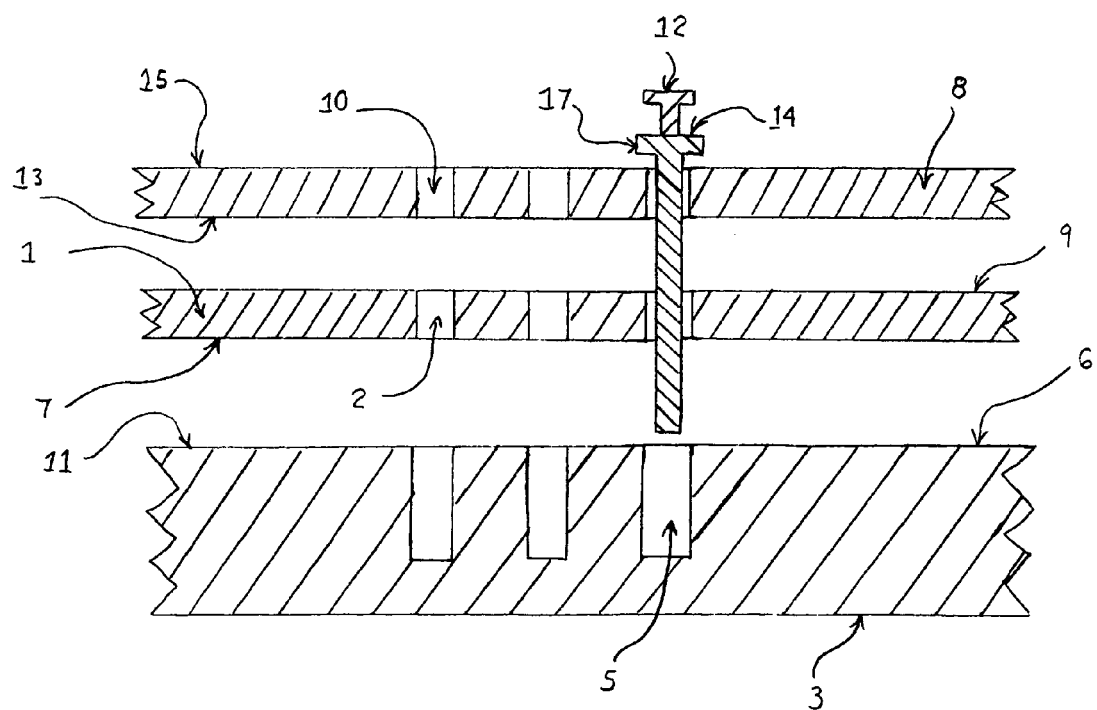
FIG. 2 is a cross-sectional view of another example of the templates disclosed herein.

According to an optional example, a second template 8 may be arranged over the top surface 9 of the first template 1 as shown in FIG. 2. Similar to the first template 1, the second template 8 defines a plurality of openings 10 that extend through the full width of the template 8 from a top surface 15 of the template 8 to a bottom surface 13 of template 8. The second template 8 is positioned so that the openings 10 are aligned with the openings 2 of the first template 1. The bottom surface 13 of the second template 8 may, or may not, contact the top surface 9 of the first template 1. The second template 8 and/or the first template 1 may be provided with an attachment mechanism such as a clamp to securely engage the template 8 with the template 1. In another embodiment, a male/female interlocking profile may be provided at the periphery of template 8 and template 1. Alternatively, adhesive tape may be applied to the template 8 and the template 1 to releasably secure the template 1 to the template 8.

A punch or needle 14 that holds a tissue sample (which may be the same or different from the punch or needle 4 used to bore the receptacle holes) is inserted through the complementary openings 10 and 2. Typically, the punch or needle does not penetrate the plane 11 of the first surface 6 of the recipient block 3. The stylet 12 disposed within the hollow channel of the needle or punch 14 then is advanced to expel or eject the tissue sample from the needle or punch and into the receptacle hole 5. The punch or needle 14 then is retracted. This procedure may be repeated as often as necessary to insert tissue specimens into as many of the receptacle holes 5 as desired. Transparent adhesive tape may be used to retain the tissue specimens in their respective receptacles and to indicate those receptacles that have already received a tissue specimen. Such a transparent adhesive tape may be an adhesive film from an adhesive-coated tape sectioning system.

Although FIG. 1 depicts using a template to form receptacle holes in the recipient block, the receptacle holes may be formed without the use of template. In this embodiment, a template is only used as a guide for introducing the samples into the already-formed receptacle holes similar to the process shown in FIG. 2. However, only a single template may be necessary for inserting the sample according to this embodiment.

The use of a template(s) as a guide to insert the tissue specimen assists in aligning each tissue specimen in a substantially vertical direction within the recipient block relative to the plane 11 of the first surface 6 of the recipient block 3. Without the template, the tissue specimens often are inserted at an unacceptable angle relative to the plane 11 of the first surface 6 of the recipient block 3. Such angled tissue specimens result in non-uniform cross-sections slides when the recipient block is sectioned. The second template 8 particularly assists in ensuring that the needle or punch remains perpendicular to the surface of the recipient block and that the tissue specimens are properly aligned.

The number of openings 2, 10 in the templates 1, 8 may be any desired amount that is sufficient to provide guides for boring the receptacle holes and inserting the tissue specimens. For example, the number of openings 2, 10 may range from 10 to 1000, more particularly 25 to 100. The openings may be arranged into any array pattern on the template. Illustrative array patterns include squares (for instance, 5×5 or 10×10) or rectangles as a single array, or as sub arrays in a square or rectangle pattern as desired. Each individual opening 2, 10 can be formed into any shape that can receive a punch or tissue donor needle. In a specific example, the openings 2, 10 are circular. The size of the openings 2, 10 should be sufficient to accommodate the needle or punch. The diameter of the circular openings may range, for instance, from about 0.6 to about 5 mm, more particularly about 1.6 to about 4.1 mm, and most particularly about 1.5 to about 4 mm. The openings 2, 10 in the templates 1, 8 may be the same size or shape or they may differ in size and/or shape. The openings in the template(s) may be spaced apart from each other by about 1.5 mm to about 4 mm.

The template(s) may be made from any suitable material that provides the desired structural characteristics. For example, the template(s) may be rigid, flexible or resilient. Such materials include various plastics (acrylics or plexiglas (i.e., poly(methyl methacrylate sheet)), metals and glass. Transparent materials are desirable. The template can be a pre-existing product such as a processing cassette (commercially available from R. A. Lamb), or it may be specifically fashioned for the purpose of making tissue microarrays. Processing cassettes, however, are not preferred since they do not have sufficient edges to assist in securing the template to the recipient block. The thickness of the template(s) may range from about 1 to about 20 mm, more particularly about 5 to about 15 mm. In one example, the thickness of template 1 may be about 2 to about 5 mm thicker compared to the thickness of the template 8.

The recipient block may be formed from a rigid embedding medium such as paraffin, gelatin, a plastic or a medium for making cryoarrays as described in detail below. The recipient block should be sufficiently thick (e.g., about 10 to about 25 mm) so that the receptacle holes do not extend through the entire width of the recipient block.

The punch or needle 4, 14 may be provided with a protrusion(s) 16, 17, respectively. The protrusion(s) 16, 17 may assume any shape such as a circular shoulder or boss, a flange, or a pin. The protrusion(s) 16, 17 has at least one dimension that is greater than the largest dimension of the template openings 2, 10. In one approach, the protrusion(s) 16, 17 is a circular shoulder or boss that has a diameter greater than the diameter of the template openings 2, 10. In another approach, the protrusion(s) 16, 17 is a flange that extends past the outer edge of the template openings 2, 10. The protrusion(s) 16, 17 is a depth-stop that prevents the punch or needle from extending too far.

For example, in FIG. 1 the protrusion 16 engages the top surface 9 of template 1 and thus stops any further motion of the punch or needle 4. Consequently, the uniformity of the depth of the receptacle holes 5 can be easily controlled by selecting the appropriate distance for the location of the protrusion 16 along the axial length of the punch or needle 4. In particular examples, the depth of each of the receptacle holes is substantially uniform and can be, for instance, about 2 to about 20 mm, more specifically about 2 to about 8 mm. If the receptacle holes are cylindrical in shape, they may have a diameter of about 1.5 to about 4 mm.

In FIG. 2 the protrusion 17 engages the top surface 15 of the second template 8 and thus stops any further motion of the punch or needle 14. In particular, the protrusion 17 can prevent misplacing samples at incorrect depths in the receptacle holes. Consequently, the uniformity of the placement depth of the samples in the receptacle holes can be easily controlled by selecting the appropriate distance for the location of the protrusion 17 along the axial length of the punch or needle 14.

The same punch or needle can be used for both boring of the recipient block receptacles 5 and for introducing the sample into the recipient block receptacle 5. Thus, a simplified system is provided that does not require two separate punches or needles.

However, it may be desirable for the tissue specimens punched from the tissue donor block to fit more securely in the recipient block receptacles 5 that are formed to receive them. If the tissue donor punch has the same inner and outer diameters as the recipient block punch, then the tissue specimen will be formed by the inner diameter of the tissue donor punch, and the recipient receptacle will be formed by the outer diameter of the recipient punch. This discrepancy will provide a receptacle that is slightly larger in diameter than the donor tissue cylinder. Hence, the recipient punch may have a smaller diameter than the donor tissue punch. The recipient punch will therefore form a cylindrical receptacle (having a diameter corresponding to the outer diameter of recipient punch) that is substantially the same diameter as the tissue specimen, which is formed with a diameter that is determined by the inner diameter of the tissue donor punch.

In particular examples, the tissue specimen is obtained by boring an elongated sample, such as a cylindrical core, from donor tissue, and placing the donor tissue in a receptacle of complementary shape, such as cylindrical core, in the recipient array. The elongated tissue sample can be taken from a region of interest of the tissue specimen, and the size of the sample is small enough that the characteristic being analyzed is substantially homogenous throughout the small sample. Regions of interest of the tissue specimen may be located by positioning a thin section slide over the donor block, to align structures of interest in the thin section slide with corresponding tissue specimens in the donor block. The thin section slide can be obtained by initially slicing and staining a section from the donor block prior to coring of the donor block.

According to a particular example, the sample is a cylindrical specimen punched from the tissue specimen embedded in a tissue donor block, wherein the cylindrical specimen is about 2 to about 12 mm long, and has a diameter of about 0.5 to about 4 mm. In specific examples, the cylindrical specimen diameter is less than about 4 mm, more particularly about 1.5 to about 2 mm. The sample is preferably preserved in a manner (such as a frozen state, ethanol or formalin fixation) that does not interfere with analysis of nucleic acids, and the sample can therefore be subjected to any type of molecular analysis, such as any type of molecular analysis based on isolated DNA or RNA.

Illustrative types of samples include tumors, normal tissues, biopsy specimens, cells cultured in vitro, plant material, bacteria, yeast or any other form of specimen that requires microscopic examination. The biological specimen may be any type of specimen that can be placed in a tissue donor block. The tissue donor block may be a block of paraffin in which a biological specimen has been embedded. An example of a tissue donor block is shown in FIG. 1 of PCT Publication WO 01/42796.

In particular examples, different tissue specimens may be obtained from different tissue donor blocks and inserted into a single recipient block. In another variant, comparative specimens may be placed in the recipient block that are from different stages in development of a tumor, different types of tumors; and/or different stages in progression of a biologically dynamic tissue (such as uterine endometrial tissue at different days during a menstrual cycle).

The template methods described herein may be performed manually by hand. For example, suitable handheld punches or tissue donor needles are commercially available such as biopsy tools for skin and needles from the instruments commercially available from Beecher Instruments under the trade designations ATA-27 automated arrayer and MTA-II manual tissue arrayer. The template(s) may be arranged in its appropriate position by hand. The recipient punch or needle then may be inserted and withdrawn by hand through the openings in the template(s) to make the receptacle cores. The punch or tissue donor needle containing the tissue specimen is subsequently inserted into the openings of the template(s). The stylet may be pushed by hand through the punch or tissue donor needle to expel the tissue specimen into the receptacle hole. Although only a single punch or tissue donor needle is shown in FIGS. 1 and 2, a plurality of punches or tissue donor needles could be inserted simultaneously through the template(s) and into the recipient block.

The template methods also can be performed using various tissue arraying apparatus. Such apparatus typically have punch units and platforms for holding and retrieving recipient blocks and tissue donor blocks. Example of tissue arraying apparatus are shown in U.S. Pat. No. 6,699,710, PCT Publication WO 01/42796, U.S. Pat. No. 6,468,783, U.S. Pat. No. 6,383,801, and U.S. Pat. No. 6,103,518, and are commercially available from Beecher Instruments under the trade designations ATA-27 automated arrayer and MTA-II manual tissue arrayer.

Figure 3:
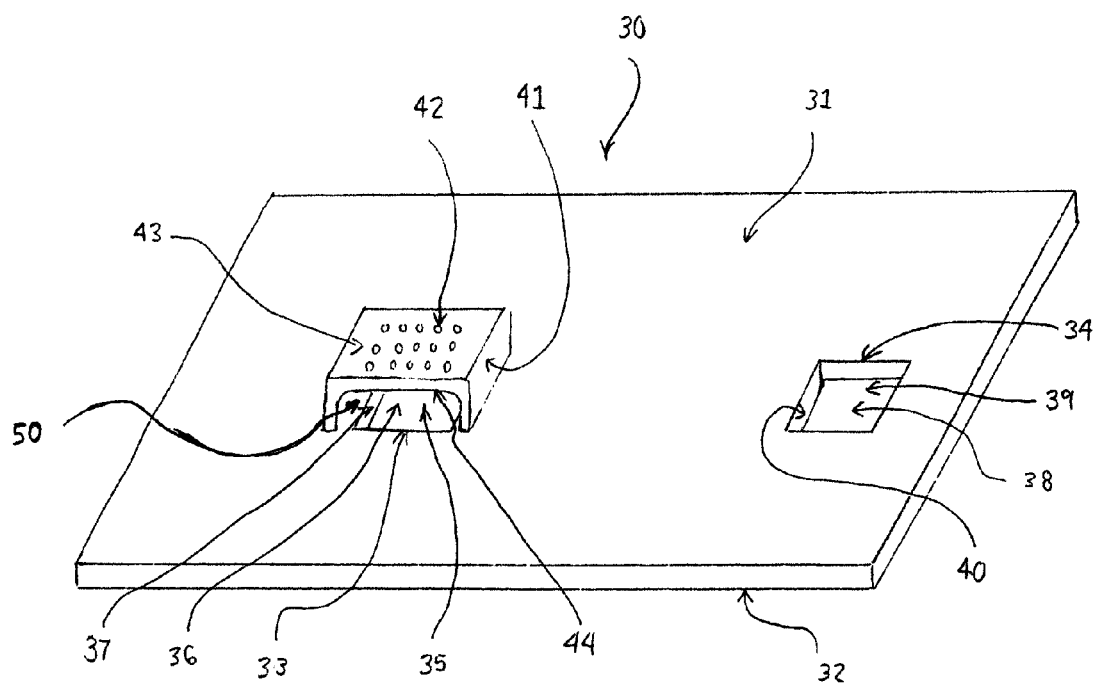
FIG. 3 is a perspective view of one example of the platform disclosed herein.

Another illustrative example of a device that utilizes a template is shown in FIG. 3. A platform 30 is provided that defines a first surface 31 and an opposing second surface 32. The platform may also include a region for retaining at least one tissue donor block and a region for retaining at least one recipient block. Alternatively, the platform may include only a region for retaining at least one recipient block (the tissue donor block is located somewhere other than on the platform). Although only a single holder for a tissue donor block and a single holder for a recipient block are shown in FIG. 3, the platform could be designed to accommodate a plurality of tissue donor blocks and recipient blocks. In the specific example shown in FIG. 3, the platform 30 includes a first region 33 for retaining a recipient block and a second region 34 for retaining a tissue donor block. The first region 33 includes a first cavity 35 for receiving a recipient block. The first cavity 35 is defined by a floor 36 and sidewalls 37. The second region 34 includes a second cavity 38 for receiving a tissue donor block. The second cavity is defined by a floor 39 and sidewalls 40. Rather than cavities, the first and second regions 33, 34 could include areas on the first surface 31 that are outlined by raised ridges (not shown) that can retain the recipient block and the tissue donor block.

The platform 30 also includes a raised template 41 that is disposed above the first cavity 35 for the recipient block. The raised template 41 defines a plurality of openings 42 that extend through the full width of the template 41 from a top surface 43 of the template 41 to a bottom surface 44 of template 41. The raised template 41 may be releasably or permanently secured to the first surface 31 of platform 30. The first cavity 35 and the raised template 41 together form a slot 50 into which a recipient block can be inserted. An array then is formed in the recipient block using the raised template 41 as a guide as described above in connection with FIGS. 1 and 2.

The platform 30 can be used, for example, as the platform in the apparatus shown in FIGS. 7-9 of PCT Publication WO 01/42796, FIGS. 1, 2 and 13-17 of U.S. Pat. No. 6,699,710. Such platforms can be coupled to an x-y positioning device to align the platform and the recipient block in a desired located relative to a punch or needle.

A further embodiment of a template process involves the use of at least one template to construct a cryoarray. Illustrative examples of cryoarrays are described in US-2003-0054342-A1, which is incorporated herein by reference. Such processes involve providing a recipient block having a plurality of receptacle holes, placing one or more liquid samples in one or more of the receptacle holes (usually one sample per well) via a template guide, then freezing the samples in the sample wells to produce a loaded array. This loaded array can then be sectioned into a plurality of cryosections such that the samples are at addressable locations in the cryosections. The template (especially a chilled metal template) placed over the recipient block can assist to maintain the freezing temperature of the cyroarray while the cyroarray is being prepared.

More particularly, cryoarrays are formed as a block (referred to as a cryoblock) of a solid embedding medium with receptacle holes substantially perpendicular to one surface of the block, into which the samples will be placed. The substrate for the cryoarray is an embedding medium that is sufficiently rigid ("frozen") at least at the temperature at which the block is prepared that it can be sectioned to provide individual cryosections for analysis (e.g., sectioned using a cryostat). Rigidity is a relative term, and in this context refers to sufficient rigidity to maintain samples within the array in substantially the same position in cryosections as they were in the cryoblock, so that individual features remain reliably addressable. A mold or cast form (e.g., made from aluminum or some other metal) could be used to mold or cast the recipient block. The recipient block also may be placed on a base plate for transfer into a cryostat. In one example, a base plate/recipient block/template assembly may be placed into a cryostat. The samples can be introduced into the recipient block via the template to form a cryoarray.

In general, the embedding medium is such that the samples can be bound to it, in order to secure the sample into the well and maintain its placement when the cryoblock is sectioned. Thus, the embedding medium of the cryoblock may be different for different samples, and either the solution in which the sample is suspended or the substance of the cryoblock can be adjusted in minor ways to ensure that such binding occurs. For some embodiments, optimal binding of the sample to the block substrate is achieved by bringing the osmolarity or osmolality of the liquid sample into relative parity with the osmolarity or osmolality of the block. In some embodiments, a gelling agent (such as a gelatin, agarose, acrylamide, or other gelling agent) is added to the samples to stabilize their binding to the block when they are frozen.

One specific example of a particularly appropriate embedding material is optical cutting temperature (OCT) embedding compound (available from a number of sources, including CryoGel OCT, available from Instrumedics Inc., Hackensack, N.J.). Additional cryoblock materials for certain embodiments include gelatin (for instance, as found in Jell-O™), pudding, agarose, polyacrylamide, wax (particularly waxes that have appropriate wetting properties so that a cryoblock constructed from such wax would be both sectionable and able to bond to the sample), and other cross-linked or matrix-forming substrates, including other polysaccharide gels or matrixes.

Sample-receiving receptacle holes in cryoarrays can be produced by any method that places elongated, substantially columnar sample-receiving receptacles into the recipient block. In some embodiments, this involves placing a plurality of pin-like intrusions into the recipient block before it is frozen, then removing the pins to leave a plurality of receptacle holes in the recipient block. Alternatively, receptacle holes can be drilled or punched into a frozen block of embedding medium. For example, a template can be used as a guide for boring the receptacle holes as described above. In some embodiments, the receptacle holes have a bottom, in that there are not holes that pass through the entire thickness of the cryoblock.

The microarrays prepared according to the methods and devices described herein include a plurality of samples arrayed in assigned locations. The assigned locations may be identified by a coordinate system as described in U.S. Pat. No. 6,699,710 and PCT Publication WO 01/42796. The coordinates may be of a substantially uniform matrix of rows and columns. A plurality of cross-sections of the microarrays can be obtained so that each cross-section contains a plurality of samples that maintain their assigned locations. For example, the microarray may be sliced with a microtome to obtain a plurality of consecutive or sequential cross-sections. In one variant, an adhesive film is placed over the top surface of the three-dimensional, sample-filled recipient block, and then a 4-8 µm thick section of the recipient block is cut transverse to the longitudinal axis of the cylindrical sample to produce a thin microarray section (containing sample sections in the form of a disk). The thin microarray section is transferred to a conventional specimen slide. The microarray section is adhered to the slide. The film is then peeled away from the underlying microarray section to expose it for biological analysis. The number of consecutive arrays that can be cut from the recipient block can range from the hundreds to the thousands, such as from about 100 to about 2000. Each consecutive array section includes samples that are substantially identical to the corresponding samples in the other array sections.

The microarrays can be used in a wide variety of analyses. For example, a different biological analysis may be performed on consecutive microarray cross-sections to determine if there are correlations between the results of the different analyses at corresponding locations of the array. Analyses that may be performed on the samples include laboratory analyses and clinicopathological characterization of the sample. Examples of laboratory analyses include immunohistochemistry, cytohistochemistry, histochemistry, in situ hybridization for DNA and/or RNA, laser capture microdissection, infrared and Ramen spectroscopy, confocal fluorescent imaging, immunoblotting and any methodology that can be applied to a tissue (or plant) section presented on a solid substrate. A different histological analysis may be performed on each section, for example by using different monoclonal antibodies that recognize distinct antigens, or a combination of antigenically distinct monoclonal antibodies and nucleic acid (e.g. RNA and DNA) probes on sequential sections. The result of each distinct histological analysis in each position of the array is compared, for example to determine if a tissue that expresses an estrogen receptor also has evidence that a particular oncogene has been activated. The presence or absence of the estrogen receptor and oncogene can then be correlated with clinical or pathological information about the tissue (such as the presence of metastatic disease or the histological grade of a tumor). This simultaneous parallel analysis of multiple specimens helps clarify the inter-relationship of multiple molecular and clinical characteristics of the tissue.

A typical application of tissue microarrays in cancer research and product development is the analysis of several hundred breast tumors from patients at different stages of disease development (normal breast, atypia, in situ cancer, invasive cancer, metastases) to identify the specific step at which gene alterations take place, as well as the frequency of these alterations. In another example, tissue microarrays can be constructed from tissue materials in a retrospective study design, where one can immediately correlate the expression of a molecular marker with poor prognosis. Furthermore, tissue microarrays can be used to screen many different diseases at once, such as multiple different tumor types, non-malignant tissues, and normal tissues and cells.

Having illustrated and described the principles of the disclosed methods and devices, it will be apparent that these methods and devices may be modified in arrangement and detail without departing from such principles.

What is claimed is:

1. A device for preparing an array of samples, comprising:
at least one tissue microarray recipient block having a thickness, wherein the recipient block comprises an embedding medium and includes a plurality of receptacle holes in the embedding medium that do not extend through the entire thickness of the recipient block;
a platform defining (i) a first surface, and (ii) a first cavity formed in the first surface and configured to retain the at least one recipient block;
a raised template defining an array of openings, secured to the first surface of the platform and positioned above the first cavity configured to retain the recipient block and a second template positioned over the raised template, the second template defining an array of openings, the second template openings being aligned with the openings of the raised template, each of said templates being supported by at least two support elements such that the second template clamps the raised template to the first surface and such that the raised template and the first cavity form a slot adapted to receive the recipient block, wherein the template openings are adapted to guide a needle or punch into at least one of the receptacle holes.

2. The device of claim 1, wherein the openings of the template are circular and have a diameter of about 1.5 mm to about 4.0 mm, and the openings of the template are spaced apart from each other by about 1.5 mm to about 4.0 mm.

3. The device of claim 1, wherein the raised template includes from 10 to 1000 openings.

4. The device of claim 1, wherein the embedding medium is sliceable by a microtome.

5. The device of claim 1, wherein the raised template is permanently secured to the first surface of the platform.

6. The device of claim 1, wherein the first surface also includes a region that retains at least one donor block.

7. The device of claim 1, wherein the first cavity defines a floor and sidewalls.

8. The device of claim 1, wherein the raised template is a metal template.

9. The device of claim 1, wherein the array of openings are aligned with the plurality of receptacle holes.

10. The device of claim 1, wherein the receptacle holes have a depth of 2 to 20 mm.

11. The device of claim 1, wherein the recipient block comprises a cryoarray.

12. The device of claim 1, wherein the embedding medium comprises a rigid material selected from paraffin, gelatin, a plastic, or a cryoarray medium.

13. The device of claim 1, wherein the samples are solid samples.

14. The device of claim 1, wherein the samples are biological tissue samples.

15. The device of claim 1, wherein the samples are frozen samples.

16. A device for preparing an array of samples, comprising:
a platform defining (i) a first surface, (ii) a first cavity formed in the first surface and retaining at least one tissue microarray recipient block having a thickness, wherein the recipient block comprises an embedding medium and includes a plurality of receptacle holes in the embedding medium that do not extend through the entire thickness of the recipient block, and (iii) a region located on the first surface and configured to retain at least one tissue donor block;
a raised template defining an array of openings, secured to the first surface of the platform and positioned above the first cavity configured to retain the recipient block and a second template positioned over the raised template, the second template defining an array of openings; the second template openings being aligned with the openings of the raised template; each of said templates being supported by at least two support elements such that the second template clamps the raised template to the first surface and such that the raised template and the first cavity form a slot adapted to receive the recipient block, wherein the template openings are adapted to guide a needle or punch into at least one of the receptacle holes.

* * * * *